(12) United States Patent
Ochoa

(10) Patent No.: US 10,207,203 B2
(45) Date of Patent: Feb. 19, 2019

(54) GAS TRAY EXTRACTION PROCESSES

(71) Applicant: Baker Hughes Incorporated, Houston, TX (US)

(72) Inventor: Brian Ochoa, Hannover (DE)

(73) Assignee: BAKER HUGHES, A GE COMPANY, LLC

( * ) Notice: Subject to any disclaimer, the term of this patent is extended or adjusted under 35 U.S.C. 154(b) by 250 days.

(21) Appl. No.: 15/218,353

(22) Filed: Jul. 25, 2016

(65) Prior Publication Data

US 2018/0023356 A1    Jan. 25, 2018

(51) Int. Cl.
| | | |
|---|---|---|
| G01N 33/00 | (2006.01) | |
| B01D 19/00 | (2006.01) | |
| G01N 33/24 | (2006.01) | |
| E21B 21/01 | (2006.01) | |

(52) U.S. Cl.
CPC ..... *B01D 19/0031* (2013.01); *B01D 19/0036* (2013.01); *B01D 19/0042* (2013.01); *E21B 21/01* (2013.01); *G01N 33/24* (2013.01)

(58) Field of Classification Search
CPC ... E21B 21/067; E21B 49/086; G01N 33/241; G01N 33/2823; G01N 2001/2267; B01D 19/00; B01D 19/0042
See application file for complete search history.

(56) References Cited

U.S. PATENT DOCUMENTS

| | | | |
|---|---|---|---|
| 2,923,151 A | 2/1960 | Engle et al. | |
| 4,578,579 A | 3/1986 | Dion | |
| 4,904,603 A | 2/1990 | Jones et al. | |
| 5,090,256 A | 2/1992 | Issenmann | |
| 5,199,509 A | 4/1993 | Wright et al. | |
| 5,447,052 A | 9/1995 | Delaune et al. | |
| 6,234,258 B1* | 5/2001 | Karigan | E21B 21/062 166/267 |
| 7,465,426 B2* | 12/2008 | Kerherve | B01D 19/0005 422/68.1 |
| 8,536,524 B2 | 9/2013 | Pomerantz et al. | |
| 8,714,246 B2 | 5/2014 | Julian et al. | |
| 2006/0093523 A1 | 5/2006 | Norman | |
| 2010/0089120 A1 | 4/2010 | Hanson | |
| 2015/0260703 A1 | 9/2015 | Mitchell et al. | |

FOREIGN PATENT DOCUMENTS

CN    101470105    12/2007

OTHER PUBLICATIONS

Caroli et al., "Quantitative Mud Gas Reconciliation with Downhole Fluid Analysis: Towards a Quantitative Fluid Log," SPE Paper 166246 (2013), 37 pages.
Roberts et al, "New System Provides Continuous Quantitative Analysis of Gas Concentration in the Mud During Drilling," SPE Paper 19562 (1991), 10 pages.
Amen, Randall M., "Quantifying Hydrocarbon Shows Using On-Line Gas Referencing," SPWLA 35th Annual Logging Symposium, Jun. 19-22, 1994, 11 pages.

(Continued)

*Primary Examiner* — Blake A Tankersley
(74) *Attorney, Agent, or Firm* — Shawn Hunter

(57) ABSTRACT

Systems and methods for mud logging wherein the effectiveness of a primary gas trap is measured during operation.

17 Claims, 1 Drawing Sheet

(56) References Cited

OTHER PUBLICATIONS

Breviere et al., "Gas Chromatography-Mass Spectrometry (GCMS)—A New Wellsite Tool for Continuous C1-C8 Gas Measurement in Drilling Mud—Including Original Gas Extractor and Gas Line Concepts. First Results and Potential," SPWLA 43rd Annual Logging Symposium, Jun. 2-5, 2002, 10 pages.

Austin, Ellis H., Chapter 4: Mud Logging, Drilling Engineering Handbook (1983), pp. 122-173.

Anonymous, "Overflow, Heated, Ultrasonic and Air Vented Mud Gas Extraction System," Published at IPCOM000245458D on Mar. 10, 2016.

\* cited by examiner

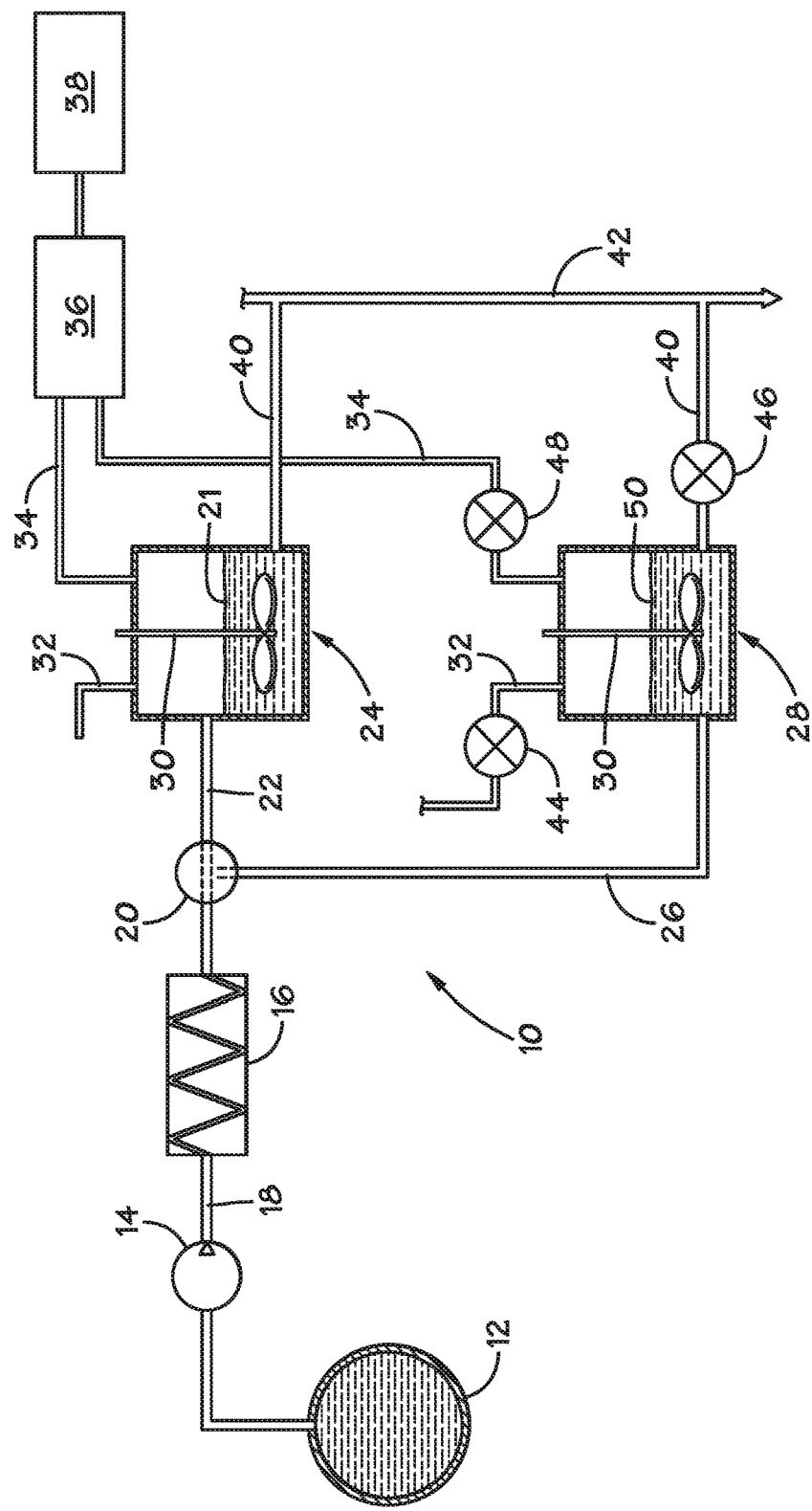

GAS TRAY EXTRACTION PROCESSES

BACKGROUND OF THE INVENTION

1. Field of the Invention

The invention relates generally to systems and methods for efficiently extracting gas from drilling mud. In particular aspects, the invention relates to systems and methods for improving gas trap efficiency.

2. Description of the Related Art

A standard drilling process includes circulating drilling mud through a well to establish well control, cutting removal and bit cooling. When drilling through a medium containing gas, condensate or oil, hydrocarbons are released from the penetrated interval. The released hydrocarbons are then transported to the surface in the drilling mud. Additional hydrocarbons may be released into the mud from oil or condensate due to changing conditions from subsurface to surface. The amount of released hydrocarbon gas, not bound or trapped in or on the cuttings, depends on the porosity, permeability and hydrocarbon saturation of the formation.

Mud logging is a commonly used service in the hydrocarbon industry and involves the extraction and measurement of hydrocarbons which are dissolved in the drilling mud. Measurements are typically conducted at surface during drilling operations using a mass spectrometer, a gas chromatograph or a combination of both. Of particular relevance to the industry are the hydrocarbons that are released from penetrated lithological units and recorded at surface once they become evaporated into gaseous phase under atmospheric conditions. Ideally, the measured hydrocarbons are only from the milled formation and can, therefore, provide highly valuable information when correlated with corresponding depths and corrected for artifacts.

Depending on the mud and hydrocarbon combination, the amount of hydrocarbons in solution may vary, and single components may have a different solubility. Conventional hydrocarbon extraction is accomplished by feeding mud through a vessel having a mechanical agitator and sucking the evaporated hydrocarbons from the headspace of a gas trap device toward a measuring unit. Based upon the measured hydrocarbon compositions and the fluid type used for the drilling operation (i.e., water-based mud, oil-based mud, synthetic oil-based mud) features like gas/oil contacts and oil/water contacts can be determined.

SUMMARY OF THE INVENTION

The present invention relates to systems and methods for extraction of gas as well as conducting proper quantitative analysis of the hydrocarbons (C1 to C8) present in the mud. A gas extraction efficiency model is used to identify the gas extraction efficiency of the gas trap for each type of hydrocarbon. The gas extraction efficiency model can be adjusted in the field to account for the types and amount of gas in the drilling mud, the type of drilling mud being used and other operational parameters, such as flow rates, temperatures and extraction pressures of the system.

In a particular embodiment, a gas extraction efficiency base is determined by comparing gas extracted during continuous operation with gas extracted in a batch process of a known and constant volume of mud in a secondary gas trap that runs in parallel with the primary gas trap. The secondary gas trap will extract ideally, with similar or different gas extraction methods, all the extractable gas from a particular volume of mud.

A gas extraction system is described which includes a primary gas trap which is operable to receive a first amount of drilling mud and remove hydrocarbon gas from the first amount of drilling mud. The system also includes a secondary gas trap which is operable to remove all or substantially all of the extractable gas from a second volume of drilling mud. A gas analyzer is used to measure the amounts of gas removed by the primary and secondary gas traps as well as to compare them.

A method is described of determining the efficiency of a primary gas trap used in mud logging. In an exemplary method, hydrocarbon gas is removed from a first amount of drilling mud using a first gas trap. Hydrocarbon gas is then completely removed from a second amount of drilling mud using a secondary gas trap. The amount of hydrocarbon gas removed from both gas traps is then measured and compared to determine the efficiency of the primary gas trap, relative to the secondary gas trap, in removing hydrocarbon gas from the drilling mud.

BRIEF DESCRIPTION OF THE DRAWINGS

For a thorough understanding of the present invention, reference is made to the following detailed description of the preferred embodiments, taken in conjunction with the accompanying drawings, wherein like reference numerals designate like or similar elements throughout the several FIGURES of the drawings and wherein:

FIG. 1 is a schematic illustration of an exemplary mud gas extraction system constructed in accordance with the present invention.

DETAILED DESCRIPTION OF THE PREFERRED EMBODIMENTS

FIG. 1 illustrates an exemplary mud gas extraction system 10 which is used to collect drilling mud from a wellbore annulus (or other location) and extract gas from the collected drilling mud. The mud gas extraction system 10 draws drilling mud from a mud suction sampling line 12. The mud suction sampling line 12 is typically placed as close as possible to the annulus of a wellbore. From there, the mud and hydrocarbon mixture is pumped through the mud gas extraction system 10 by fluid pump 14 at typical rates between about 1 liter/minute and about 10 liters/minute. The fluid pump 14 draws mud from the mud suction sampling line 12 and flows the mud to mud heater 16 via mud conduit 18. The mud heater 16 is operable to heat drilling mud. The mud heater 16 is operably connected with a three-way valve 20. A first mud transmission conduit 22 extends from the three-way valve 20 to a primary gas trap 24. A second mud transmission conduit 26 extends from the three-way valve 20 to a secondary gas trap 28. The three-way valve 20 can be manually operated or operated automatically. Further, the motive force for actuating the three-way valve 20 may be electrical, hydraulic or pneumatic. The three-way valve 20 can switch between the first mud transmission conduit 22 and the second mud transmission conduit 26 at any desired or optimal moment during the drilling (i.e., When there is high gas reading, when there is a change of section or at any particular time that the operator desires to corroborate the gas extraction efficiency). Each of the primary and secondary gas traps 24, 28 include a rotary agitator 30 which is useful for agitating drilling mud within the gas trap. Each of the primary and secondary gas traps 24, 28 also includes an air inlet 32 through which outside air can enter the gas trap. Gas exhaust lines 34 extend from each of the primary and secondary gas traps 24, 28 to a pneumatic unit 36 which is operable to pull the gas (via vacuum pump) out of either of the first and secondary gas traps 24, 28. The pneumatic unit 36 is operably associated with a gas analyzer 38, which may be in the form of a gas chromatograph suitable for analyzing gas removed from drilling mud by the gas traps 24, 28. The gas analyzer 38 may be made up of one or two separate analysis units, depending upon the capability of the pneumatic unit 36. If the pneumatic unit 36 is capable of multiplexing between multiple exhaust line 34, then only a single analysis unit is required. Gas is provided by the pneumatic unit 36 to the gas analyzer 38 from the primary gas trap 24 most of the time and switched to provide gas from the secondary gas trap 28 only at times when gas is to be analyzed from there. If the gas analyzer 38 includes dual analysis units, the pneumatic unit 36 can continuously provide gas from the primary gas trap 24 to one analysis unit and the gas from the secondary gas trap 28 to a second analysis unit. Preferably, the gas analyzer 38 is capable of measuring the amounts of each hydrocarbon (C1 to C8) removed by each of the gas traps 24, 28. Mud exhaust lines 40 extend from each of the gas traps 24, 28 to a mud drain line 42.

The air inlet 32 of the secondary gas trap 28 is preferably provided with an air inlet valve 44 which can be opened to flow and closed against flow of air into the secondary gas trap 28. The mud exhaust line 40 of the secondary gas trap 28 preferably also includes a mud exhaust line valve 46 which can be opened to permit flow of drilling mud out of the secondary gas trap 28 or closed off to prevent such flow. The gas exhaust line 34 of the secondary gas trap 28 preferably also includes a gas exhaust line valve 48 which can be opened and closed to control the flow of gas exiting the secondary gas trap 28.

In exemplary operation of the mud gas extraction system 10, the pump 14 draws drilling mud from the mud suction sampling line 12 and transmits it to and through the mud heater 16. The three-way valve 20 directs a first amount 21 drilling mud through the first mud transmission conduit 22 to the primary gas trap 24. The primary gas trap 24 then removes gas from the drilling mud. Removed gas exits the primary gas trap 24 via the gas exhaust line 34 to the pneumatic unit 36 and gas chromatograph 38 for analysis. The amounts of each type of hydrocarbon (C1 to C8) removed from the first amount 21 of drilling mud are measured by the gas chromatograph 38. Degassed mud exits the primary gas trap 24 via mud exhaust line 40. As degassed mud exits the primary gas trap 24, additional mud to be degassed enters the primary gas trap 24 in a continuous mode.

At a point during operation, the three-way valve 20 will divert the flow of drilling mud from the first mud transmission conduit 22 to the second mud transmission conduit 26 and into the secondary gas trap 28. The secondary gas trap 28 is preferably a static gas trap which conducts a static test of drilling mud.

Preferably, the secondary gas trap 28 is cleaned and placed under a desired internal pressure prior to flowing drilling mud into the secondary gas trap 28. The secondary gas trap 28 is preferably evacuated of all gas and mud which might be remaining from prior gas removal operation. An exemplary method for doing this would be to open the gas exhaust line valve 48 and mud exhaust line valve 46 and then actuate the pneumatic unit 36 to flow compressed air into the secondary gas trap 28, cleaning all lines of gas and draining any mud in the trap. Then the mud exhaust line valve 46 is closed and the air inlet valve 44 is opened. The pneumatic unit 36 is actuated to draw fresh air into the secondary gas trap 28. The air inlet valve 44 is then closed, creating a vacuum pressure, if necessary. The secondary gas trap 28 can be depressurized to a desired internal vacuum pressure by the pneumatic unit 36.

After a second amount 50 of drilling mud is flowed into the secondary gas trap 28, the air inlet valve 44 is open, and the mud exhaust line valve 46 is closed. The secondary gas trap 28 is then actuated to extract substantially all the extractable gas from the second amount 50 of mud. Preferably, gas is extracted by agitation using the rotary agitator 30. Extraction can be assisted by increasing in temperature of the drilling mud. Extraction of gas could also be assisted by reducing pressure within the secondary gas trap 28 or by steam still, ultrasonic or microwave methods. Reduced pressure for degassing can be achieved via the air inlet valve 44 and mud exhaust line valve 46. A steam generator (not shown) of a type known in the art can be used to extract gas using steam-assisted methods. Microwave energy can be used for gas extraction as described, for example, in U.S. Pat. No. 5,447,052 ("Microwave Hydrocarbon Gas Extraction System"). Further description of degassing methods is described in "Overflow, Heated, Ultrasonic and Air Vented Mud Gas Extraction System," which is available at IP.com as Publication no. IPCOM000245458D and which is herein incorporated by reference. Following degassing, the mud exhaust valve 46 is opened and degassed mud is flowed to the mud drain line 42 via mud exhaust line 40.

Once gas has been extracted from the second amount 50 of drilling mud, separated gas is analyzed by the gas analyzer 38. Preferably, the amounts of each type of hydrocarbon (C1 to C8) removed from the second amount 50 are measured. These values are then compared to the values of hydrocarbons removed from the first amount 21 of drilling mud by the primary gas trap 24. The efficiency of the first gas trap 24 in removing gas from the first amount 21 of drilling mud can be determined via comparison to the amount of gas removed from the second amount 50 of drilling mud by the secondary gas trap 28.

The efficiency of the primary gas trap 24 is determined relative to the substantially complete efficiency of the secondary gas trap 28 in removing hydrocarbon gas from an amount of drilling mud. A gas extraction efficiency chart can be constructed that will correlate the removed gas measured under continuous operation versus the gas that should be measured as removed. In certain embodiments, the efficiency testing procedure is automated and carried out by a programmable controller which has been programmed with instructions to carry out the steps of the process. The programmable controller may be in the form of a programmable logic controller, microcontroller, embedded computer or a personal controller which is programmed with a predefined sequence of operations for conducting the efficiency testing. Also, in accordance with certain embodiments, complete degassing of a second amount 50 of drilling mud is done on a periodic basis during routine degassing of first amounts 24 by the primary gas trap 24. Extraction efficiency can be evaluated when there is a high gas reading, when there is a change of section of drilling or at any particular time that an operator desires to corroborate the gas extraction efficiency.

It should be appreciated that the invention provides a system for extracting hydrocarbon gas from amounts of drilling mud and which allows the efficiency of gas removal can be monitored during operation of the system. An exemplary system includes primary and secondary gas traps 24, 28 and a gas analyzer, such as gas chromatograph 38.

Preferably, the secondary gas trap 28 includes valves 44, 46, 48 which can be closed against flow in order to isolate an amount 50 of drilling mud and permit the secondary gas trap 28 to extract substantially all extractable gas from the amount 50 of drilling mud. The gas analyzer 38 is preferably a gas chromatograph.

It should also be appreciated that the invention provides methods for determining efficiency of a primary gas trap used in mud logging. In accordance with exemplary method, hydrocarbon gas is removed from a first amount 21 of drilling mud in the primary gas trap 24. Substantially all extractable gas is removed from a second amount 50 of drilling mud by the secondary gas trap 28. The amounts of hydrocarbon gas removed from both the first and second amounts 21, 50 of drilling mud are then measured. Typically, the amount in moles of each hydrocarbon present in the extracted gas.

Those of skill in the art will recognize that numerous modifications and changes may be made to the exemplary designs and embodiments described herein and that the invention is limited only by the claims that follow and any equivalents thereof.

What is claimed is:

1. A system for mud logging characterized by:
   a primary gas trap which receives a first amount of drilling mud and is operable to extract a first amount of hydrocarbon gas from the first amount of drilling mud;
   a secondary gas trap which receives a second amount of drilling mud and is operable to extract a second amount of substantially all extractable hydrocarbon gas from the second amount of drilling mud; and
   a gas analyzer that receives hydrocarbon gas separated from the first amount of drilling mud and from the second amount of drilling mud, the gas analyzer being operable to measure the hydrocarbon gas removed from each of the first and second amounts,
   wherein the system for mud logging compares the first amount of hydrocarbon gas extracted by the primary gas trap to the second amount of substantially all extractable hydrocarbon gas extracted by the secondary gas trap to determine a relative effectiveness for the primary gas trap.

2. The system of claim 1 further comprising:
   a mud conduit to transmit drilling mud to the primary gas trap; and
   a valve operably associated with the mud conduit to divert drilling mud to the secondary gas trap.

3. The system of claim 2 further comprising a mud heater operably associated with the mud conduit to heat drilling mud within the mud conduit.

4. The system of claim 1 further comprising:
   an air inlet for the secondary gas trap which permits outside air to enter the secondary gas trap; and
   an air inlet valve for the air inlet that permits flow of outside air into the secondary gas trap to be completely closed off.

5. The system of claim 1 wherein the gas analyzer comprises a gas chromatograph.

6. The system of claim 1 further comprising a pneumatic unit operably associated with the secondary gas trap and useful for cleaning the secondary gas trap with compressed air.

7. The system of claim 1 further comprising:
   a gas exhaust valve operably associated with the secondary gas trap for closing off flow of gas out of the secondary gas trap; and
   a mud exhaust valve operably associated with the secondary gas trap for closing off flow of mud out of the secondary gas trap.

8. A system for mud logging characterized by:
   a mud conduit to supply drilling mud from a mud line;
   a primary gas trap which receives a first amount of drilling mud and is operable to extract a first amount of hydrocarbon gas from the first amount of drilling mud;
   a secondary gas trap which receives a second amount of drilling mud and is operable to extract a second amount of substantially all extractable hydrocarbon gas from the second amount of drilling mud; and
   a gas analyzer that receives hydrocarbon gas separated from the first amount of drilling mud and from the second amount of drilling mud, the gas analyzer being operable to measure the hydrocarbon gas removed from each of the first and second amounts,
   wherein the system for mud logging compares the first amount of hydrocarbon gas extracted by the primary gas trap to the second amount of substantially all extractable hydrocarbon gas extracted by the secondary gas trap to determine a relative effectiveness for the primary gas trap.

9. The system of claim 8 further comprising a valve operably associated with the mud conduit to divert drilling mud to the secondary gas trap.

10. The system of claim 8 further comprising:
    an air inlet for the secondary gas trap which permits outside air to enter the secondary gas trap; and
    an air inlet valve for the air inlet that permits flow of outside air into the secondary gas trap to be completely closed off.

11. The system of claim 8 further comprising:
    a gas exhaust valve operably associated with the secondary gas trap for closing off flow of gas out of the secondary gas trap; and
    a mud exhaust valve operably associated with the secondary gas trap for closing off flow of mud out of the secondary gas trap.

12. The system of claim 8 further comprising a pneumatic unit operably associated with the secondary gas trap and useful for cleaning the secondary gas trap with compressed air and pull via a vacuum pump gas from each of the primary and secondary gas traps.

13. The system of claim 8 further comprising a mud heater operably associated with the mud conduit to heat drilling mud within the mud conduit.

14. A method of determining efficiency of a primary gas trap used in mud logging, the method characterized by the steps of:
    removing hydrocarbon gas from a first amount of drilling mud in the primary gas trap;
    completely removing hydrocarbon gas from a second amount of drilling mud with a secondary gas trap;
    measuring the amounts of hydrocarbon gas removed from the first amount of drilling mud and the second amount of drilling mud; and
    determining the relative effectiveness of the primary gas trap by comparing the amount of hydrocarbon gas removed from the first amount of drilling mud with the amount of hydrocarbon gas completely removed from the second amount of drilling mud.

15. The method of claim 14 wherein the step of measuring the amounts of hydrocarbon gas removed is performed by a gas chromatograph.

16. The method of claim 14 wherein the step of completely removing hydrocarbon gas from a second amount of drilling mud further comprises subjecting the second amount of drilling mud to at least one of the following: agitation, heating, depressurization, ultrasonic waves and microwaves.

17. The method of claim 14 wherein the step of completely removing hydrocarbon gas from a second amount of drilling mud further comprises isolating the second amount of hydrocarbon gas within the secondary gas trap by closing off flow of drilling mud into and out of the secondary gas trap and closing off flow of air into the secondary gas trap.

* * * * *

UNITED STATES PATENT AND TRADEMARK OFFICE
CERTIFICATE OF CORRECTION

PATENT NO. : 10,207,203 B2
APPLICATION NO. : 15/218353
DATED : February 19, 2019
INVENTOR(S) : Brian Ochoa Page 1 of 1

It is certified that error appears in the above-identified patent and that said Letters Patent is hereby corrected as shown below:

On the Title Page

In the title, Item (54) and in the Specification in Column 1, Line 1, the word "TRAY" should be --TRAP--.

Signed and Sealed this
Twenty-sixth Day of March, 2019

Andrei Iancu
*Director of the United States Patent and Trademark Office*